United States Patent [19]
Johnson et al.

[11] Patent Number: 6,010,664
[45] Date of Patent: Jan. 4, 2000

[54] OXIDATION DETECTION FOR SULFITE/SULFATE SYSTEMS

[75] Inventors: Dennis W. Johnson, Barberton; Pervaje A. Bhat, North Canton, both of Ohio

[73] Assignee: The Babcock & Wilcox Company, New Orleans, La.

[21] Appl. No.: 08/089,962

[22] Filed: Jul. 12, 1993

[51] Int. Cl.⁷ .......................... G01N 21/00; G01N 30/96; G01N 27/00; G01N 35/08

[52] U.S. Cl. ................ 422/62; 422/88; 422/98; 422/105; 422/108; 422/111; 422/172; 423/242.1; 423/243.01; 423/555; 436/55; 436/119; 436/122; 436/163

[58] Field of Search .................................... 436/119, 122, 436/55, 163; 422/62, 105, 108, 111, 88, 98, 172; 423/243.01, 555, 242.1

[56] References Cited

U.S. PATENT DOCUMENTS

| | | |
|---|---|---|
| 3,945,904 | 3/1976 | Robison . |
| 3,985,864 | 10/1976 | Vautrain et al. . |
| 4,010,239 | 3/1977 | Dor . |
| 4,021,201 | 5/1977 | Vautrain et al. . |
| 4,100,266 | 7/1978 | Smith . |
| 5,008,203 | 4/1991 | Mathews . |
| 5,168,065 | 12/1992 | Jankura et al. . |

*Primary Examiner*—Anthony C. Caputa
*Assistant Examiner*—Mark Navarro
*Attorney, Agent, or Firm*—Daniel S. Kalka; Robert J. Edwards

[57] ABSTRACT

A method for monitoring the oxidation rate in a flue gas desulfurization system having a slurry comprises locating a monitor in the system for accessing the slurry. A sample is periodically drawn from the slurry by the monitor wherein a titration is performed on each sample. The titration performed on each sample comprises adding a potassium iodate $KIO_3$ solution, a potassium iodide KI starch solution and an acid solution to the sample in the monitor for causing the sample to exhibit a color corresponding to the oxidation rate.

11 Claims, 2 Drawing Sheets

OXIDATION DETECTION FOR SULFITE/SULFATE SYSTEMS

BACKGROUND OF THE INVENTION

1. Field of the Invention

The present invention relates in general to flue gas desulfurization systems and, in particular, to a new and useful method for detecting the forced oxidation of sulfates and sulfites.

2. Description of the Related Art

In the utility industry, the burning of coal results in a major industry-wide problem due to $SO_2$ emissions. In an effort to reduce $SO_2$ emissions, desulfurization systems have been developed for removing $SO_2$. One such desulfurization system is the wet flue gas desulfurization system using forced oxidation. An in situ forced oxidation system is currently used in conjunction with limestone and lime scrubbers for converting the $SO_2$ from the flue gas to a high quality wall-board gypsum, $CaSO_4 \cdot 2H_2O$. In this system, limestone, $CaCO_3$, is reacted with the $SO_2$ and exposed to compressed air in order to maintain a 99% or higher oxidation rate for producing the commercial grade gypsum.

The removal of $SO_2$ and the production of commercial grade gypsum are directly dependent on the oxidation rate for the system. Therefore, it is important that the oxidation rate be maintained at a sufficient level. The maintaining of the oxidation rate, however, requires that the oxidation rate be monitored, using an indirect measurement method.

U.S. Pat. No. 5,168,065 describes a forced oxidation monitoring and control system.

Presently, the monitoring of oxidation rates for flue gas desulfurization systems are performed under laboratory conditions. The current monitoring methods are quite complicated and elaborate due to the laboratory-type conditions involved.

At this time, there are no known methods or systems for providing an efficient on-line monitoring of an oxidation rate for a flue gas desulfurization system.

SUMMARY OF THE INVENTION

The present invention comprises a method for monitoring the forced oxidation in a flue gas desulfurization system (FGD) such as an in situ wet scrubber. The present invention provides for a continuous direct measurement of the oxidation rate in an in situ wet scrubber by utilizing automatic titration of a slurry for the scrubber.

The present invention comprises locating a monitor in the system for accessing the slurry while periodically drawing a sample from the slurry by the monitor. A titration is performed on the sample by adding a potassium iodate $KIO_3$ solution, a potassium iodide, KI, starch solution and an acid solution to the sample in the monitor for causing the sample to exhibit a visible color corresponding to the sulfite concentration. The amount of $KIO_3$ added to cause the color change is indicative of the oxidation level.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

The present invention pertains to a wet scrubber for a flue gas desulfurization system and can be applied to any aqueous sulfite/sulfate system where the sulfite/sulfate exists in a solution with the term solution meaning to encompass both a solution or a slurry.

The present invention can be utilized in a wet scrubber that uses limestone or lime as a reagent or other types of reagents for removing $SO_2$ from the flue gas. In a flue gas desulfurization system, which utilizes a natural oxidation or a forced oxidation, $SO_2$ is removed from the flue gas through the following reactions:

(1) $SO_2(g) <==> SO_2(aq)$
(2) $SO_2(aq) + H_2O <==> HSO_3^- + H^+ <==> SO_3^= + 2H^+$
(3) $CaCO_3(s) + H^+ \rightarrow Ca^{++} + HCO_3^-$
(4) $HCO_3^- + H^+ \rightarrow CO_2(g) + H_2O$
(5) $CaSO_3 \cdot \frac{1}{2}H_2O + H^+ <==> Ca^{++} + HSO_3^- + \frac{1}{2}H_2O$
(6) $O_2(g) <==> O_2(aq)$
(7) $\frac{1}{2}O_2(aq) + HSO_3^- \rightarrow SO_4^= + H^+$
(8) $Ca^{++} + SO_4^= + 2H_2O \rightarrow CaSO_4 \cdot 2H_2O$
(9) $Ca^{++} + SO_3^= + \frac{1}{2}H_2O \rightarrow CaSO_3 \cdot \frac{1}{2}H_2O$ The absorption of $SO_2$ is shown as Reactions (1) and (2). The $SO_2$ absorption causes the dissolution of the limestone through reactions (3) and (4). The limestone neutralizes the products of Reaction (2), resulting in a consumption of $H^+$. In reaction (5), the dissolution of $CaSO_3 \cdot \frac{1}{2}H_2O$, is also a consumer of $H^+$ in the gas/liquid reaction zone of the natural oxidized scrubber and has a buffering effect which reduces the pH suppression of the limestone.

A natural oxidation occurs via Reactions (6) and (7). In flue gas desulfurization systems, the amount of natural oxidation is limited by the relative insolubility of oxygen, which is available in the flue gas at only 3–8%. The amount of oxidation that occurs is limited by the slow diffusion of oxygen to the liquid phase and by the amount of $SO_2$ absorbed. This means that the amount of natural oxidation will be higher for low sulfur flue gas desulfurization systems than for high sulfur systems operated under similar conditions.

The reaction products in controlled oxidation systems precipitate through Reactions (8) or (9). Reaction (8) is also the cause of gypsum scaling within the naturally oxidized scrubber. Gypsum scaling and poor solids settling characteristics are two of the major operation problems generally associated with natural oxidation flue gas desulfurization systems. The poor crystal habit of naturally oxidized solids is the result of co-precipitation which causes irregular needle-like crystal formations which are thixotropic in nature. This means they liquify when stirred or shaken but return to the solid state on standing. These mixed crystals as such have no commercial value, are difficult to handle, and are expensive to landfill.

Figure 1:
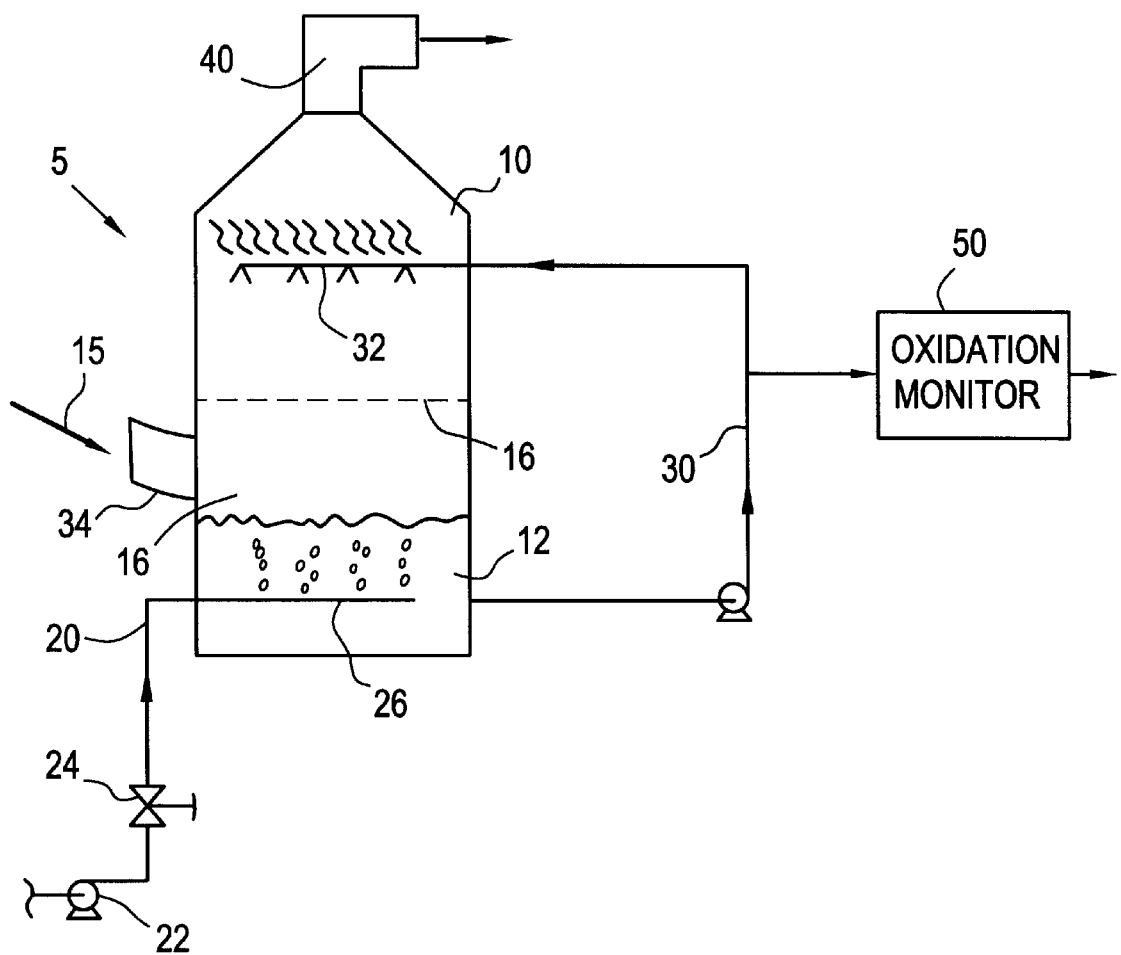
FIG. 1 is a schematic representation of the present invention in conjunction with a flue gas desulfurization system.

In a forced oxidation system, such as that shown in FIG. 1, a flue gas desulfurization system, generally designated 5, comprises a reaction tower 10 for removing $SO_2$ from a flue gas 15 emitted from a combustion source (not shown). Tower 10 is further partitioned into absorption zone 18 where the primary reaction is that of $SO_2$ absorption and reaction tank 12 where forced oxidation of the products of $SO_2$ absorption takes place.

The flue gas 15 is channeled into the absorber tower 10 through an inlet 34 in a known manner. A tray 16 is positioned beneath an array of absorber sprayers 32 in the tower 10. The nozzle sprayers 32 spray a lime or limestone slurry 12 in the tower 10 for reacting with the flue gas 15 in an absorption zone 18 of the tower 10. Oxidation air 20 is provided in the reaction tank 12 through a pump 22 and a valve 24. The oxidation air 20 is provided to the limestone slurry in the reaction tank 12 through oxidation air spargers 26. The limestone slurry from the reactor tank 12 is circulated to the tower 10 by a circulation loop 30. A flue gas outlet 40 is provided in the tower 10 for channeling the flue gas 15 after the removal of $SO_2$ from the flue gas 15.

In the forced oxidation system 5, illustrated in FIG. 1, the air 20 introduced into the reactor tank 12 causes reactions (6), (7) and (8) to dominate and produce $CaSO_4.2H_2O$ or gypsum. In this case $HSO_3^-$ (bisulfite) formed in reaction (2) is oxidized, as shown in reaction (7), and reactions (5) and (9) essentially cease to exist in the in situ forced oxidation. Therefore, the typical concentration of sulfite ($SO_3^=$) is relatively low.

However, upon the loss of forced oxidation, more liquid phase sulfite species are formed resulting in production of sulfite ($SO_3^=$) in reaction (2) and an increase in the occurrence of reactions (5) and (9) involving solid sulfite crystals and decrease in the occurrence of reaction 7 termed a loss of oxidation. When this happens, the concentration of dissolved sulfite species increases significantly.

Presently, the oxidation loss for a flue gas desulfurization system is detected remotely under laboratory conditions using a Modified Palmrose analysis. A typical Modified Palmrose analysis is summarized below as follows:

1. Extract 2 ml of slurry sample using a 1 ml automatic pipette and place in a 250 ml beaker. Add 25–50 ml distilled $H_2O$.
2. Add 5–10 ml starch solution.
3. Overtitrate with 0.125N $H_2SO_4$ by at least 5 ml but no more than 10 ml. Normally 15 ml of 0.125N $H_2SO_4$ will accomplish this.
4. Without agitating, titrate to a deep blue end point with 0.125N $KIO_3$. (Begin to stir only after about 50 percent of the $KIO_3$ has been added.)
5. Add 1–3 drops of 3 percent sodium thiosulfate and sample will become clear. If more than 3 drops are required, the end point was exceeded; start the entire test over.
6. Add several drops of methyl purple indicator.
7. Backtitrate with 0.125N NaOH to a blue-green end point. If less than 5 ml NaOH are used, start over using 5 more ml $H_2SO_4$ in step 3. If more than 10 ml NaOH are used, start over using 5 less ml $H_2SO_4$ in step 3.

The concentration of limestone ($CaCO_3$), calcium hydroxide ($Ca(OH)_2$), and calcium sulfite ($CaSO_3.\tfrac{1}{2}H_2O$) are determined by the following calculations:

8.

$$gm/l\ CaCo_3 = \frac{[(ml\ H_2SO_4 \times N\ H_2SO_4) - (ml\ NaOH \times N\ NaOH)]}{ml\ sample} 50$$

9.

$$gm/l\ Ca(OH)_2 = \frac{[(ml\ H_2SO_4 \times N\ H_2SO_4) - (ml\ NaOH \times N\ NaOH)]}{ml\ sample} 37$$

10.

$$gm/l\ CaSO_3 \cdot 1/2H_2O = \frac{(ml\ KIO_3 \times N\ KIO_3)}{ml\ sample} 64.5$$

As illustrated in FIG. 1, the present invention utilizes an oxidation monitor 50 which detects an oxidation rate for an absorber reactor 12 by locating the oxidation detector 50 in the circulation loop 30 of the absorber tower 10. The present invention provides for a slip stream filtration option and the direct titration while the $SO_2$ absorber 10 is in operation. The filtration option allows for detecting sulfite/bisulfite in the liquid phase. Liquid phase or dissolved sulfite/bisulfite detection is important, for example, in forced oxidation FGD. Normal operation in this case is with a low concentration of liquid phase sulfite/bisulfite. As described earlier, loss of oxidation results in increased liquid phase sulfite species thus for this case only liquid phase detection is necessary. For other cases such as natural or inhibited oxidation FGD, waste water treatment, etc., filtration would not be required in order to detect changes in total sulfite species including both liquid phase and solid sulfite.

Figure 2:
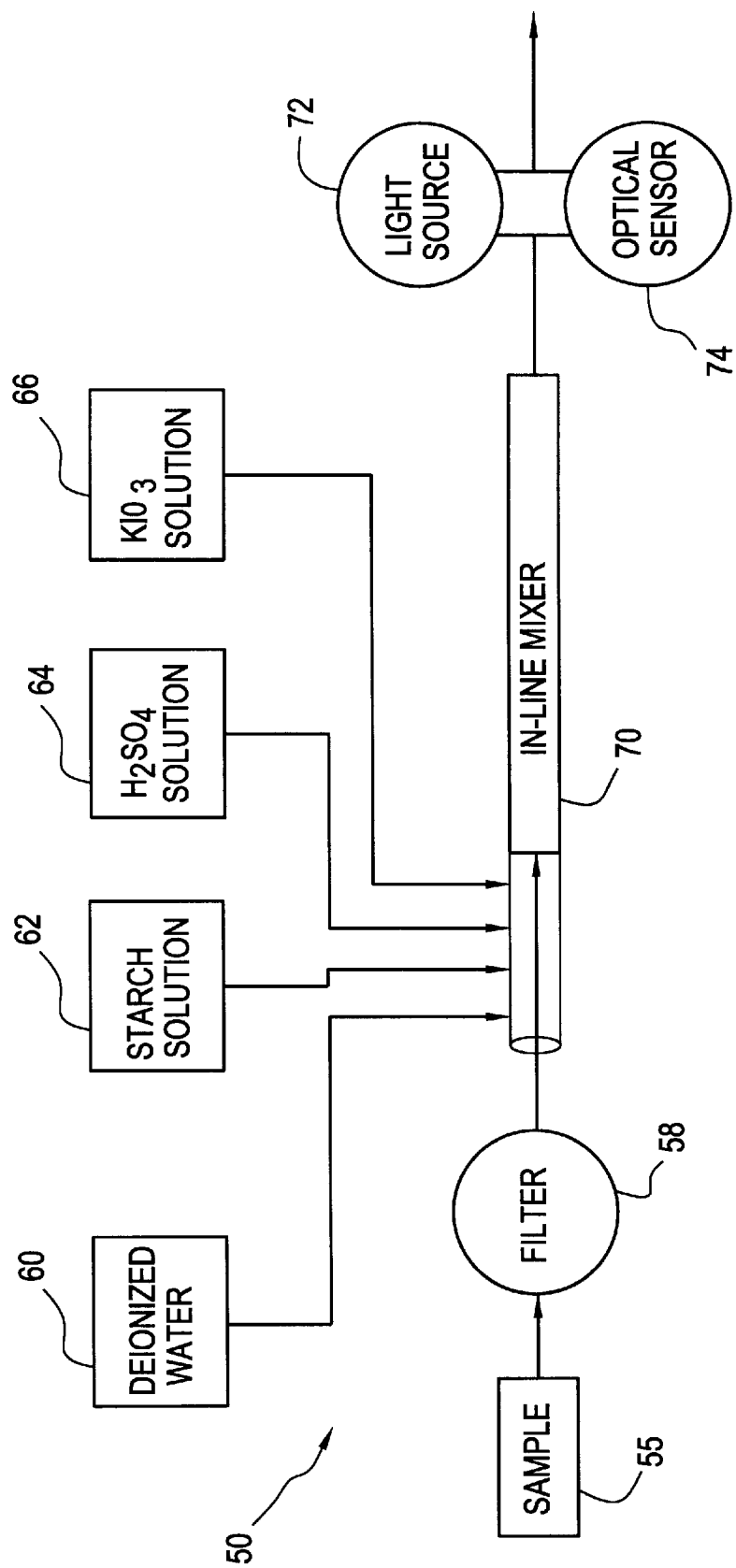
FIG. 2 is a block diagram illustrating a method according to the present invention.

FIG. 2 shows a method according to the present invention in which a slurry sample 55 is extracted from the slurry circulation loop 30 (FIG. 1) and filtered by a filtration means 58. Suitable pumps, valves, mixers and tubing are commercially available for example from the Fisher Scientific Products Catalog. After filtration, the sample 55 is subjected to a titration in the monitor 50. The titration according to the present invention is an in-line Modified Palmrose analysis comprising adding a required amount of a potassium iodate $KIO_3$ solution 66 to the sample 55 which contains a sulfate, sulfite or bisulfite. Preferably, the potassium iodate $KIO_3$ solution 66 is 0.125N which is in the range of about 0.0125 to 0.125N. Of course, the normality of the $KIO_3$ solution can vary depending upon the sulfite/bisulfite concentration.

A potassium iodide KI starch solution is also added to the sample 55. The potassium iodide starch solution 62 has a composition of about 50 to 150 gm of potassium iodide KI, about 100 to 300 gm of Thyodene, a starch solution available from Fisher Scientific Products, and, about 500 to 1500 gm of water. It is preferred that the potassium iodide KI starch solution 62 comprise 100 gm of KI, 200 gm of thiodene and 800 gm of water.

The titration of the sample 55 is performed in an acid such as a sulfuric acid $H_2SO_4$ solution 64 having a normality (N) of 0.125N for neutralizing any alkali and dissolving $CaSO_3.\tfrac{1}{2}H_2O$. Suitable titration equipment would include autotitrators employing an optic detector, e.g. a Mettler DL70 with photometric analysis.

Deionized water 60 is also added to the sample 55 and provided to an in-line mixer 70 along with the sample 55, the KI solution 62, the $H_2SO_4$ solution 64 and the $KIO_3$ solution 66. The titration of the sample 55 performed in the monitor 50 causes the sample to develop an end point of a deep blue color. After being subjected to the solutions listed above, the sample 55 is exposed to a light source 72 operating at a wavelength of about 400–500 nm and an optical sensor 74 for determining the change of color of the sample 55 or a visible light with an optical sensor to measure the intensity of the light as compared with a reference. For a continuous or batch sample when the flow of the sample and solution 62, 64, and 68 are constant relative to each other, loss of the blue color of the end point of the sample 55 indicates that there is an increase in sulfite/sulfate concentration in the slurry 12 (FIG. 1) Any spectrophotometer with a flow cell can be used or even a split beam light meter with a reference and sample using a light source operating in the visible range. Thus, the present invention provides for an automatic and accurate real time oxidation detector using a Modified Palmrose analysis. The real time indication of the oxidation status for the system allows for a more efficient flue gas desulfurization operation.

Table 1 shows results obtained from commercial FGD units. The volumes for deionized water or starch solution have not been included as they are not critical. Normally, the water volume ranges from 25–50 ml. and the starch solution ranges from 5–10 ml. Also, separate titrations can be made for determining calcium concentration and the alkaline species $CaCO_3$ and $Ca(OH)_2$.

The present invention can also be integrated into the controls of the system for automatically compensating for changes in the oxidation rate detected by the monitor or triggering an alarm for alerting the operator of a problem requiring a response.

The present invention reduces the laboratory sampling requirements associated with known oxidation rate monitoring methods by providing an in-line monitor for automatic oxidation rate detection.

The present invention reduces sampling error due to loss of temperature when removing sample. The present invention provides greater sample homogeneity and limits the loss of $CO_2(g)$ or $SO_2(g)$ to the atmosphere when sampling which affects sample equilibrium.

While a specific embodiment of the invention has been shown and described in detail to illustrate the application of the principles of the invention, it will be understood that the invention may be embodied otherwise without departing from such principles.

TABLE 1

OXIDATION DETECTOR EXAMPLE
PALMROSE ANALYSIS RESULTS

| REAGENT OXIDATION MODE | UNITS | LIMESTONE FORCED | LIMESTONE FORCED | LIMESTONE NATURAL | LIMESTONE INHIBITED | LIME FORCED | LIME FORCED | LIME NATURAL |
|---|---|---|---|---|---|---|---|---|
| NORMALITY H2SO4 | N | 0.125 | 0.124 | 0.125 | 0.10 | 0.125 | 0.125 | 0.125 |
| NORMALITY KIO3 | N | 0.0125 | 0.0125 | 0.125 | 0.10 | 0.125 | 0.125 | 0.125 |
| VOLUME SAMPLE | ml | 2.00 | 2.00 | 2.00 | 3.66 | 2.00 | 2.00 | 2.00 |
| VOLUME H2SO4 | ml | 10.00 | 15.00 | 15.00 | 20.00 | 10.12 | 10.18 | 10.56 |
| VOLUME KIO3 | ml | 0.05 | 23.10 | 10.30 | 58.00 | 0.02 | 1.85 | 21.98 |
| COMPOSITION | | | | | | | | |
| CaCO3/Ca(OH)2 | mmoles/l | 35.90 | 228.00 | 225.65 | 201.68 | 42.48 | 43.69 | 75.75 |
| CaSO3:½ H2O | mmoles/l | 0.16 | 72.10 | 536.67 | 1271.13 | 1.20 | 92.58 | 1102.20 |
| CaSO4:2 H2O | mmoles/l | 1699.74 | 949.00 | 489.78 | 171.83 | 1884.16 | 1509.01 | 210.42 |
| OXIDATION | % | 99.99 | 92.94 | 47.72 | 11.91 | 99.94 | 94.22 | 16.03 |
| CONDITION | | NORMAL | UNSTABLE | NORMAL | NORMAL | NORMAL | UNSTABLE | NORMAL |

In Table I, the limestone and lime forced oxidized modes include an example of normal operation at or near 100% oxidation and unstable operation (which would require operator interaction) less than 99% oxidation. The present invention monitors the change from normal to unstable operation to alert the operator through a signal which may be electronic, video or audio, in real time of an operational problem. It also lets the operator know when normal operation is regained. Finally, the present invention can readily interface with microprocessor controls to correct an unstable condition without operator interaction.

For the inhibited oxidation mode, the invention can be used to monitor oxidation rate directly in order to optimize use of the oxidation inhibiting chemical, e.g., sulfur, thiosulfate, EDTA, formate, etc.

The present invention allows for an early indication of operational problems caused by a loss in the oxidation rate and allows for the operation of the system to be improved by increasing byproduct quality. The present invention also allows for the optimization of the operation parameters of the system such as oxidation air flow, reagent utilization, etc. which result in reduced operating costs.

What is claimed is:

1. An on-line method for detecting and monitoring oxidation in a flue gas desulfurization system, the method comprising the steps of:

locating an oxidation monitor in a circulation loop of an absorber tower of the system for accessing a sample solution;

drawing the sample solution to the oxidation monitor;

performing an iodiometric titration on the sample in the oxidation monitor;

causing the sample to exhibit a color change; and determining a sulfite/bisulfite concentration based on color change.

2. The method according to claim 1, wherein the performing step comprises the steps of adding a predetermined amount of potassium iodate ($KIO_3$) solution, a predetermined amount of potassium iodide (KI) starch solution, and a predetermined amount of an acid solution to the sample in the monitor.

3. The method according to claim 2, wherein the acid solution comprises a sulfuric acid $H_2SO_4$ solution.

4. The method according to claim 3, wherein the potassium iodide KI starch solution comprises potassium iodide KI, starch and water.

5. The method according to claim 4, wherein a deionized water is also added to the sample for performing the titration.

6. The method according to claim 1, wherein the sample is filtered after being drawn.

7. The method according to claim 1, wherein the titration further comprises subjecting the sample to a light source.

8. The method according to claim 1, wherein the titration further comprises subjecting the sample to an optical source.

9. The method according to claim 4, wherein the potassium iodide further comprises 50 to 150 gm of potassium iodide, 100 to 300 gm of starch and 500 to 1500 gm of water.

10. The method according to claim 3, wherein the sulfuric acid $H_2SO_4$ solution is 0.125N.

11. The method according to claim 2, wherein the potassium iodate $KIO_3$ solution is 0.0125N to 0.125N.

* * * * *